(12) United States Patent
Weigand et al.

(10) Patent No.: US 10,077,274 B2
(45) Date of Patent: Sep. 18, 2018

(54) UV-CURING-COMPATIBLE PHOTOCHROMIC FUSED NAPHTHOPYRANS

(71) Applicant: RODENSTOCK GMBH, München (DE)

(72) Inventors: Udo Weigand, München (DE); Herbert Zinner, Rohrbach (DE); Yven Rohlfing, München (DE)

(73) Assignee: RODENSTOCK GMBH, München (DE)

( * ) Notice: Subject to any disclaimer, the term of this patent is extended or adjusted under 35 U.S.C. 154(b) by 282 days.

(21) Appl. No.: 14/899,389

(22) PCT Filed: Jun. 12, 2014

(86) PCT No.: PCT/EP2014/001602
§ 371 (c)(1),
(2) Date: Dec. 17, 2015

(87) PCT Pub. No.: WO2014/202194
PCT Pub. Date: Dec. 24, 2014

(65) Prior Publication Data
US 2016/0152629 A1    Jun. 2, 2016

(30) Foreign Application Priority Data

Jun. 17, 2013 (DE) .......... 10 2013 010 032
Nov. 26, 2013 (DE) .......... 10 2013 019 706

(51) Int. Cl.
*C07D 493/04* (2006.01)
*C08K 5/1575* (2006.01)
(Continued)

(52) U.S. Cl.
CPC .......... *C07D 493/04* (2013.01); *C08K 5/1575* (2013.01); *G02B 5/23* (2013.01); *G02C 7/022* (2013.01); *G02C 7/102* (2013.01)

(58) Field of Classification Search
CPC ... C07D 311/92; C07D 493/08; C07D 493/04
See application file for complete search history.

(56) References Cited

U.S. PATENT DOCUMENTS 3,567,605 A    3/1971    Becker
5,645,767 A    7/1997    Van Gemert
(Continued)

FOREIGN PATENT DOCUMENTS

EP    1978022 A1    10/2008
EP    2305768 A1    4/2011
(Continued)

OTHER PUBLICATIONS

ISA / EP, International Search Report and Written Opinion prepared for PCT/EP2014/001602 dated Sep. 9, 2014.

*Primary Examiner* — Ramsey E Zacharia
(74) *Attorney, Agent, or Firm* — McDonald Hopkins LLC

(57) ABSTRACT

The present invention relates to UV-curing-compatible photochromic single- or double-fused naphthopyrans of the general formulae (I) or (II) and the use thereof in plastics of all kinds, particularly for ophthalmic purposes. The photochromic compounds according to the invention are characterized by their excellent UV-curing compatibility, i.e. they remain undamaged—incorporated, for example, in an acrylate monomer matrix with UV initiator—by a free-radical polymerization of the matrix initiated by strong UV light. The photochromic dyes according to the invention, by means of suitable choice of substituents, are in addition characterized by two distinct absorption bands of the open form in the visible wavelength range, i.e. two conventional (Continued)

photochromic dyes, each having one discrete absorption band, can be replaced with a molecule of this type.

5 Claims, 2 Drawing Sheets

(51) Int. Cl.
  *G02C 7/02* (2006.01)
  *G02C 7/10* (2006.01)
  *G02B 5/23* (2006.01)

(56) References Cited

U.S. PATENT DOCUMENTS

| | | |
|---|---|---|
| 5,698,141 A | 12/1997 | Kumar |
| 5,723,072 A | 3/1998 | Kumar |
| 5,955,520 A | 9/1999 | Heller et al. |
| 6,018,059 A | 1/2000 | Chan |
| 6,022,495 A | 2/2000 | Kumar |
| 6,379,591 B1 | 4/2002 | Breyne et al. |
| 6,426,023 B1 | 7/2002 | Chang et al. |
| 6,506,538 B1 | 1/2003 | Breyne et al. |
| 6,558,583 B2 | 5/2003 | Breyne et al. |
| 2010/0230648 A1* | 9/2010 | Izumi .................. C07D 311/78 252/586 |

FOREIGN PATENT DOCUMENTS

| | | |
|---|---|---|
| WO | 98/32037 A1 | 7/1998 |
| WO | 99/15518 A1 | 4/1999 |
| WO | 2009/024271 A1 | 2/2009 |
| WO | 2013/045086 A1 | 4/2013 |

* cited by examiner

UV-CURING-COMPATIBLE PHOTOCHROMIC FUSED NAPHTHOPYRANS

This application is a 35 U.S.C. 371 national stage filing and claims priority to PCT Application PCT/EP2014/001602 entitled "UV-CURING-COMPATIBLE PHOTOCHROMIC FUSED NAPHTHOPYRANS," filed Jun. 12, 2014, which claims the benefit of German Applications: 102013010032.1, filed Jun. 17, 2013; and 102013019706.6, filed Nov. 26, 2013, each of which are incorporated by reference herein in its entirety.

The present invention relates to UV-curing-compatible photochromic single- or double-fused naphthopyrans of the general formulae (I) or (II) and the use thereof in plastics of all kinds, particularly for ophthalmic purposes. The photochromic compounds according to the invention are characterized by their excellent UV-curing compatibility, i.e. they remain undamaged—incorporated, for example, in an acrylate monomer matrix with UV initiator—by a free-radical polymerization of the matrix initiated by strong UV light. The photochromic dyes according to the invention, by means of suitable choice of substituents, are in addition characterized by two distinct absorption bands of the open form in the visible wavelength range, i.e. two conventional photochromic dyes, each having one discrete absorption band, can be replaced with a molecule of this type. They also have a very good lifetime at a very high level of performance. They may be used in all types of plastics.

There has long been knowledge of various dye classes which, on irradiation with light of particular wavelengths, especially solar rays, reversibly change color. This is because these dye molecules are converted by light energy to an excited state ("open form"), which they leave again in the event of interruption of the energy supply and revert to their starting state. These photochromic dyes include various pyran systems which have already been described in the prior art with different base systems and substituents.

Pyrans, especially naphthopyrans and larger ring systems derived from these, are currently the class of photochromic compounds which has been the subject of the most work. Even though a patent was first filed as early as 1966 (U.S. Pat. No. 3,567,605), it was not until the 1990s that compounds which appeared suitable for use in ophthalmic lenses were developed. Suitable classes of pyran compounds are, for example, the 2,2-diaryl-2H-naphtho[1,2-b]pyrans or the 3,3-diaryl-3H-naphtho[2,1-b]pyrans, which, in open, excited forms, exhibit various darkening colors from yellow to red-violet.

When this bridging is prepared only via one atom, the result is a five-membered ring fused to the naphthopyran. For example, a carbon atom ("indeno-fusion") is found in U.S. Pat. No. 5,645,767, U.S. Pat. No. 5,723,072 and U.S. Pat. No. 5,955,520 and an oxygen atom in U.S. Pat. No. 6,018,059.

In U.S. Pat. No. 5,723,072, an unsubstituted, mono- or disubstituted heterocyclic ring may additionally be fused to this base system on the g, h, i, n, o or p side of the indenonaphthopyran. Accordingly, indeno[2,1-f]naphtho[1,2-b]pyrans with a very wide range of variation of possible substituents are disclosed.

WO 96/14596, WO 99/15518, U.S. Pat. No. 5,645,767, WO 98/32037 and U.S. Pat. No. 5,698,141 also describe photochromic indenofused naphthopyran dyes derived from 2H-naphtho[1,2-b]pyran, the compositions comprising them and a process for preparation thereof. In U.S. Pat. No. 5,698,141, an unsubstituted, mono- or disubstituted heterocyclic ring may additionally be fused to this base system on the g, h, i, n, o or p side of the indenonaphthopyran. The substituent list, which is very extensive in each case, also includes quite specific spiro compounds, more particularly those systems with a spiro heterocyclic group in which, including the spiro atom at the 13 position of the base system, a 5- to 8-membered ring which always contains two oxygen atoms is present. A further configuration of the spiro ring can be found in JP 344762/2000.

If this bridging is generated via two atoms, a fused six-membered ring results having diverse possibilities just for C, O and N. Compounds having a lactam bridge are described in U.S. Pat. No. 6,379,591 and compounds having an unsubstituted $CH_2$—$CH_2$ bridge and also an additional fused heterocycle are described in U.S. Pat. No. 6,426,023. U.S. Pat. No. 6,506,538 describes the carbocyclic analog compounds in which the hydrogen atoms in the bridge can be replaced by OH, $(C_1$-$C_6)$-alkyl or $(C_1$-$C_6)$-alkoxy or two hydrogen atoms on a carbon atom can be replaced by =O. U.S. Pat. No. 6,022,495 describes many compounds, including those having an O—$CR^1R^2$ bridge, likewise WO 2009/024271 and WO 2013/045086.

When this link is generated by three atoms, the result is a fused 7-membered ring with very many possible variations through insertion of heteroatoms. Compounds having a $CH_2$—$CH_2$—$CH_2$ bridge are described in U.S. Pat. No. 6,558,583. Here too the hydrogen atoms in the bridge can be replaced by OH, $(C_1$-$C_6)$-alkyl or $(C_1$-$C_6)$-alkoxy or two hydrogen atoms on a carbon atom can be replaced by =O. Given the same substitution pattern, they absorb at a shorter wavelength than the fused 6-membered rings.

The different photochromic dyes available in the prior art, however, have disadvantages which, in the case of use in sun-protection lenses, significantly impair the wear comfort of the eyeglass wearer. Firstly, the dyes have insufficient long-wave absorption in the excited state and in the unexcited state. Secondly, there is frequently too high a thermal sensitivity of the darkening, and lightening may at the same time be too slow. Furthermore, the dyes available in the prior art often have an inadequate lifetime and hence allow only a short service life of the sun-protection lenses. The latter manifests itself in rapidly declining performance and/or intense yellowing.

Common to the photochromic dyes in the prior art mentioned above is that they exhibit only one absorption band of the open form in the visible wavelength range. In order to achieve darkening phototropic glasses in neutral colors—i.e. in gray or brown hues—a balancing process between the different photochromic dyes of a mixture is required with respect to rate of lightening, lifetime and spectral excitation properties, so that the phototropic glass has the same hue at each time point of the darkening and lightening cycle. It would therefore be extremely desirable to be able to dispense with this balancing process.

Finally, many photochromic compounds disclosed in the prior art exhibit insufficient UV-curing compatibility, i.e. they do not remain undamaged—incorporated, for example, in an acrylate monomer matrix with UV initiator—by a free-radical polymerization of the matrix initiated by strong UV light.

Therefore, it is the object of the present invention to provide novel photochromic dyes which make it possible to achieve darkening phototropic glasses in neutral colours—i.e. in gray or brown hues—with only one such photochromic dye, wherein the dyes should also be characterized by excellent UV-curing compatability. Such photochromic dyes, moreover, should be characterized by the combination of a long-wave absorption maximum of the closed form with a steep edge to the visible wavelength range, high darkening performance, very rapid lightening reaction and very good light stability.

This object is achieved by the embodiments characterized in the claims.

In particular, photochromic fused naphthopyrans are provided according to the general formulae (I) or (II):

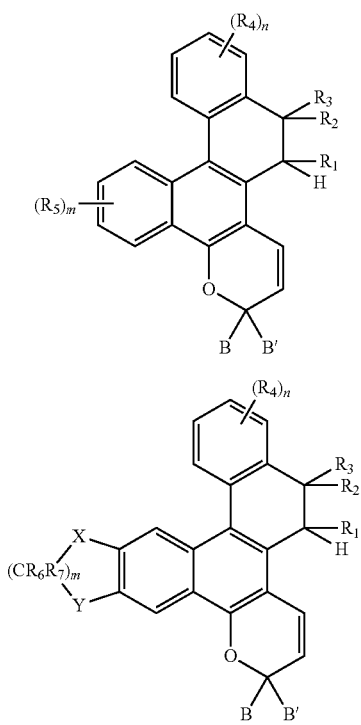

where the residues $R_3$, $R_4$ and $R_5$ are each mutually independently a substituent selected from the group α, consisting of a hydrogen atom, a $(C_1-C_6)$-alkyl residue, a $(C_1-C_6)$-thioalkyl residue, a $(C_3-C_7)$-cycloalkyl residue which may have one or more heteroatoms such as O or S, a $(C_1-C_6)$-alkoxy residue, a hydroxyl group, a trifluoromethyl group, bromine, chlorine, fluorine, an unsubstituted, mono- or disubstituted phenyl, phenoxy, benzyl, benzyloxy, naphthyl or naphthoxy residue, wherein the substituents may in turn be selected from the group α; where n, if not 0, is an integer from 1 to 4;

or two residues $R_4$ form a fused benzene ring, which may be unsubstituted, mono- or disubstituted, wherein the substituents may in turn be selected from the group α;

or two residues $R_5$ form a fused benzene ring, which may be unsubstituted, mono- or disubstituted, wherein the substituents may in turn be selected from the group α;

and where the residues $R_1$ and $R_2$ are each mutually independently a $(C_1-C_6)$-alkyl residue or an unsubstituted, mono- or disubstituted phenyl residue, wherein the substituents may in turn be selected from the group α; and with the proviso that at least one of the residues $R_1$ or $R_2$ is an unsubstituted, mono- or disubstituted phenyl residue;

and where X and Y are mutually independently selected from the group consisting of —O—, —S—, —N(C$_1$-C$_6$)-alkyl, —NC$_6$H$_5$—, —CH$_2$—, —C(CH$_3$)$_2$— or —C(C$_6$H$_5$)$_2$—;

and where the residues $R_6$ and $R_7$ are each mutually independently a substituent selected from the group α; preferably a hydrogen atom, a $(C_1-C_6)$-alkyl residue, a $(C_3-C_7)$-cycloalkyl residue or a phenyl residue;

m, if not 0, is an integer from 1 to 4, preferably 1 or 2;

or two or more adjacent —CR$_6$R$_7$ moieties are part of a fused benzene ring, which may be unsubstituted, mono- or disubstituted, wherein the substituents may in turn be selected from the group α;

or X and/or Y together with the respective adjacent —CR$_6$R$_7$ moiety is a fused benzene ring, which may be unsubstituted, mono- or disubstituted, wherein the substituents may in turn be selected from the group α;

and where B and B' are a mutually independently selected from one of the following groups a) or b), where
a) is a mono-, di- and trisubstituted aryl residue, wherein the aryl residue is phenyl, naphthyl or phenanthryl and
b) is an unsubstituted, mono- and disubstituted heteroaryl residue, wherein the heteroaryl residue is pyridyl, furanyl, thienyl, benzofuranyl, benzothienyl, 1,2,3,4-tetrahydrocarbazolyl and julolidinyl;

wherein the substituents of the aryl and heteroaryl residues in a) and b) are selected from the group α or from the group χ consisting of amino, mono-$(C_1-C_6)$-alkylamino, di-$(C_1-C_6)$-alkylamino, phenethenyl unsubstituted, mono- or disubstituted on the phenyl ring, unsubstituted, mono- or disubstituted (phenylimino)methylene, unsubstituted, mono- or disubstituted (phenylmethylene)imino and unsubstituted, mono- or disubstituted mono- and diphenylamino, piperidinyl, 3,5-dimethylpiperidinyl, N-substituted piperazinyl, pyrrolidinyl, imidazolidinyl, pyrazolidinyl, indolinyl, morpholinyl, 2,6-dimethylmorpholinyl, thiomorpholinyl, azacycloheptyl, azacyclooctyl, unsubstituted, mono- or disubstituted phenothiazinyl, unsubstituted, mono- or disubstituted phenoxazinyl, unsubstituted, mono-, di- or trisubstituted 9,10-dihydroacridinyl, unsubstituted, mono- or disubstituted 1,2,3,4-tetrahydroquinolinyl, unsubstituted, mono- or disubstituted 2,3-dihydro-1,4-benzoxazinyl, unsubstituted, mono- or disubstituted 1,2,3,4-tetrahydroisoquinolinyl, unsubstituted, mono- or disubstituted phenazinyl, unsubstituted, mono- or disubstituted carbazolyl, unsubstituted, mono- or disubstituted 1,2,3,4-tetrahydrocarbazolyl and unsubstituted, mono- or disubstituted 10,11-dihydrodibenz[b,f]azepinyl, wherein the substituent(s) may in turn be mutually independently selected from the group α;

or wherein two directly adjacent substituents of the aryl and heteroaryl residues in a) and b) are a V—(CR$_8$R$_9$)$_p$—W moiety, where p=1, 2 or 3, the residues $R_8$ and $R_9$ are each mutually independently a substituent selected from the group α, and also V and W are mutually independently selected from the moieties —O—, —S—, —N(C$_1$-C$_6$)-alkyl, —NC$_6$H$_5$—, —CH$_2$—, —C(CH$_3$)$_2$— or —C(C$_6$H$_5$)$_2$—;

or two or more adjacent —CR$_8$R$_9$ moieties are part of a fused benzene ring, which may be unsubstituted, mono- or disubstituted, wherein the substituents may in turn be selected from the group α;

or V and/or W together with the respective adjacent —CR$_8$R$_9$ moiety is a fused benzene ring, which may be unsubstituted, mono- or disubstituted, wherein the substituents may in turn be selected from the group α, In a preferred embodiment of the present invention, the residue $R_3$ in the above formulae (I) and (II) is selected from a hydrogen atom, a $(C_1-C_6)$-alkyl residue, a $(C_3-C_7)$-cycloalkyl residue or a phenyl residue.

The residue $R_2$ in the formulae (I) and (II) is preferably the unsubstituted, mono- or disubstituted phenyl residue relating to this.

Preferred photochromic naphthopyrans according to the present invention have the formula (II).

In the formula (II), both X and Y are particularly preferably O (oxygen). In another embodiment, X can be $CH_2$ and Y can be O or Y can be $CH_2$ and X can be O.

In a further preferred embodiment of the present invention, the photochromic naphthopyrans have the formula (III) below.

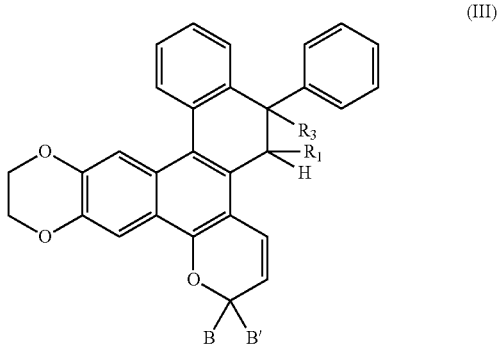

(III)

where the residue $R_1$ is a ($C_1$-$C_6$)-alkyl residue or a phenyl residue;
the residue $R_3$ is hydrogen, a ($C_1$-$C_6$)-alkyl residue or a phenyl residue;
and the residues B and B' are as defined above.

The molecular structure of the compounds according to the invention are based on a dihydrophenanthrene subunit (with the substituents $R_1$ to $R_4$ in the formula figures). Both a further benzene ring (with the substituents $R_5$ or the substituent group X—$(CR_6R_7)_m$—Y) or a 1,4-benzodioxane ring (see formula (III)) is fused, and a photolabile pyran unit (with the substituents B and B') is attached, to a benzene ring of this dihydrophenanthrene subunit. The pyran unit is responsible for the photochromic character since the bond between the oxygen of the pyran unit and the carbon atom with the substituents B and B' is broken reversibly by excitation with long-wave UVA light, whereby a colored merocyanine system is formed.

The surprising finding underlying the present invention is that, in contrast to the closest prior art (U.S. Pat. No. 6,506,538), the compounds according to the invention—incorporated, for example, in an acrylate monomer matrix with UV initiator—remain undamaged by a free-radical polymerization of the matrix initiated by strong UV light. This excellent UV compatibility is the result of the introduction according to the invention of at least two substituents ($R_1$ and $R_2$)—at least one of which is an unsubstituted or substituted phenyl residue—into the dihydrophenanthrene subunit of the molecule. Photochromic dyes having interesting spectral properties are thereby accessible which, incorporated in an acrylate matrix for example, have outstanding stability both with respect to the polymerization conditions and to the lifetime.

In addition, the compounds according to the invention, by means of suitable choice of substituents, have a distinct double absorption band of the open form in the visible wavelength range. One band has an absorption maximum of >500 nm, while the maximum of the second band lies in the shorter-wave visible range (400-500 nm). Due to the latter band, it is possible with the present invention to dispense with yellow- or orange-darkening photochromic dyes in phototropic dye mixtures. This is important on the one hand for polymer systems in which these yellow- and orange-darkening dyes—owing to their different molecular structure compared to the longer-wave absorbing violet- and blue-darkening dyes—have an insufficient lifetime or are accompanied by other disadvantages. On the other hand it is possible for the first time with some of the photochromic dyes according to the invention—to achieve darkening phototropic glasses in neutral colors—i.e. in gray or brown hues with only one photochromic dye, which glasses are produced by UV curing. The cumbersome balancing process between the different photochromic dyes of a mixture with respect to rate of lightening, lifetime and spectral excitation properties required to date is thus eliminated, so that the phototropic glass has the same hue at each time point of the darkening and lightening cycle.

Moreover, since the compounds according to the invention have high optical clarity (i.e. high transmission in the unexcited state) and very good light stability, they are eminently suitable for use in phototropic glasses.

Furthermore, the compounds according to the invention are completely colorless in the unexcited state (i.e. without esthetically disruptive yellow hue since the absorption of the closed form is limited to the UV range) and have a very good lifetime.

Figure 1:
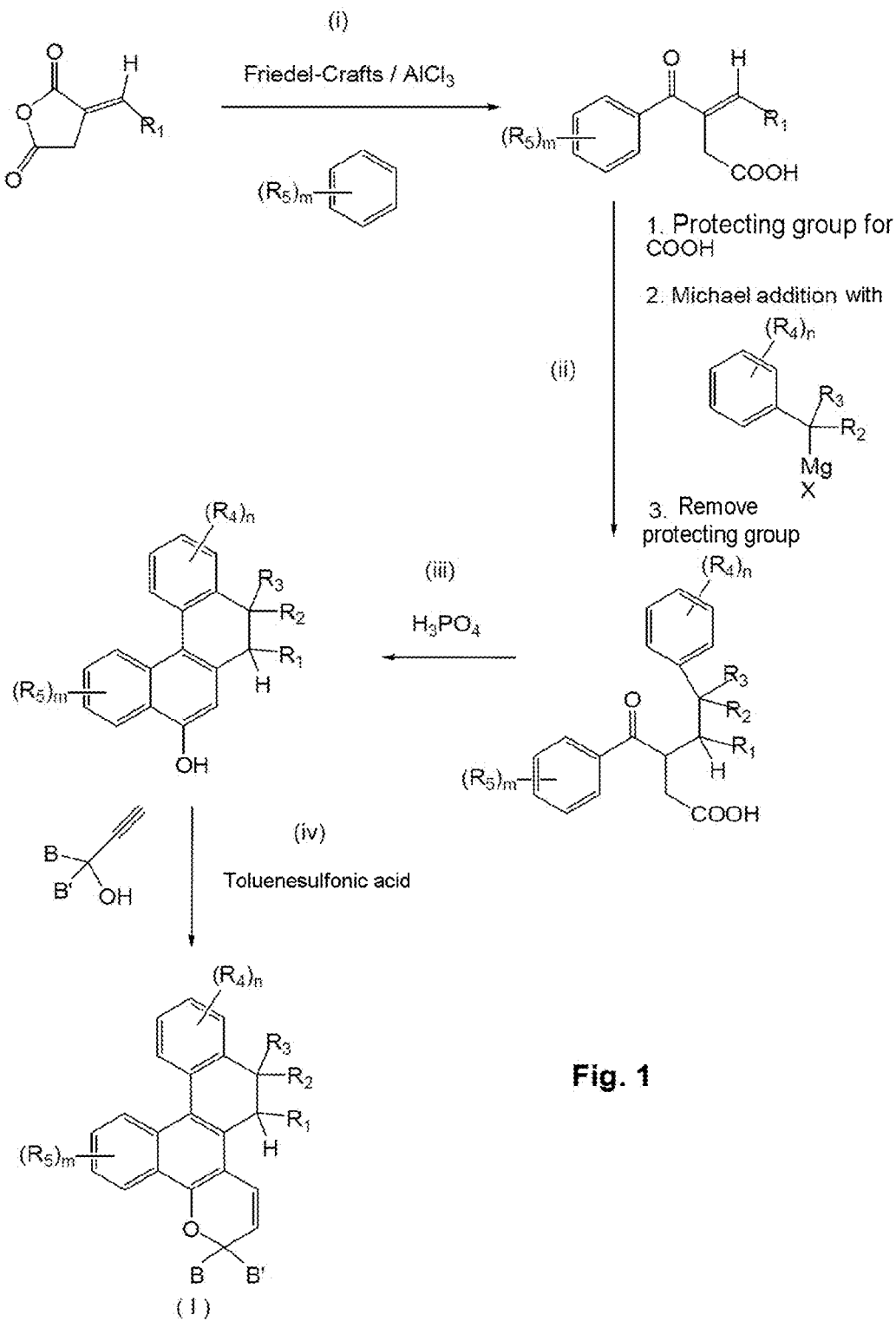
FIG. 1 shows a corresponding synthetic scheme for preparing the compounds according to the invention.

Particularly preferred compounds of the present invention are:

3,3-bis(4-methoxyphenyl)-6,7-ethylenedioxy-13-phenyl-14-methyl-13,14-dihydro-naphtho[2,1-d]naphtho[1,2-b]pyran (=inventive compound 1)

3,3-bis(4-methoxyphenyl)-6,7-ethylenedioxy-13-phenyl-13,14-dimethyl-13,14-dihydro-naphtho[2,1-d]naphtho[1,2-b]pyran (=inventive compound 2)

3,3-bis(4-ethoxyphenyl)-6,7-ethylenedioxy-13-phenyl-14-methyl-13,14-dihydro-naphtho[2,1-d]naphtho[1,2-b]pyran 3,3-bis(4-ethoxyphenyl)-6,7-ethylenedioxy-13-phenyl-13,14-dimethyl-13,14-dihydro-naphtho[2,1-d]naphtho[1,2-b]pyran 3-(4-methoxyphenyl)-3-phenyl-6,7-ethylenedioxy-13-phenyl-14-methyl-13,14-dihydro-naphtho[2,1-d]naphtho[1,2-b]pyran 3-(4-methoxyphenyl)-3-phenyl-6,7-ethylenedioxy-13-phenyl-13,14-dimethyl-13,14-dihydro-naphtho[2,1-d]naphtho[1,2-b]pyran (=inventive compound 3)

3-(4-ethoxyphenyl)-3-phenyl-6,7-ethylenedioxy-13-phenyl-14-methyl-13,14-dihydro-naphtho[2,1-d]naphtho[1,2-b]pyran 3-(4-ethoxyphenyl)-3-phenyl-6,7-ethylenedioxy-13-phenyl-13,14-dimethyl-13,14-dihydro-naphtho[2,1-d]naphtho[1,2-b]pyran 3-(4-butoxyphenyl)-3-phenyl-6,7-ethylenedioxy-13-phenyl-14-methyl-13,14-dihydro-naphtho[2,1-d]naphtho[1,2-b]pyran 3-(4-butoxyphenyl)-3-phenyl-6,7-ethylenedioxy-13-phenyl-13,14-dimethyl-13,14-dihydro-naphtho[2,1-d]naphtho[1,2-b]pyran In a further preferred embodiment, the residues B and B' in the above formulae (I), (II) and (III) are mutually independently selected from the group a), as defined above.

Particular preference is given to mono-, di- and trisubstitued aryl residues, wherein the aryl residue is a phenyl residue.

If two or more adjacent —CR$_6$R$_7$ moieties in the formula (II) are part of a fused benzene ring, which may be unsubstituted, mono- or disubstituted, wherein the substituents may in turn be selected from the group α, they are preferably in the form of the structural unit below:

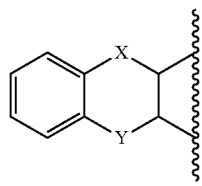

If in the formula (II), X and/or Y together with the respective adjacent —CR$_6$R$_7$ moiety is a fused benzene ring, which may be unsubstituted, mono- or disubstituted, wherein the substituents may in turn be selected from the group α, it is/they are preferably in the form of the structural unit below, in which X is preferably O:

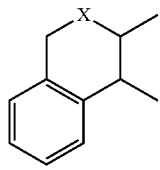

The substituents of the group χ which have nitrogen atoms or bear amine groups are attached via the latter to the phenyl, naphthyl or phenanthryl residue of the group a).

With regard to the substituents of the group V—(CR$_8$R$_9$)$_p$—W moiety which may be attached to the phenyl, naphthyl or phenanthryl residue of the group a) for the residues B and B', if two or more adjacent carbon atoms of this V—(CR$_8$R$_9$)$_p$—W moiety are each mutually independently part of a benzo ring system fused thereto, this means that the two methylene carbon atoms (—CH$_2$—CH$_2$—) are then part of a fused ring system. When, for example, two or three benzo rings are fused, it is possible, for example, for the following structural units as shown below to be present:

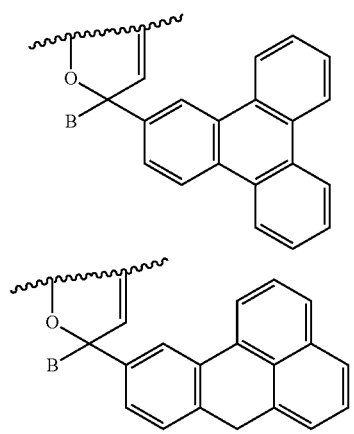

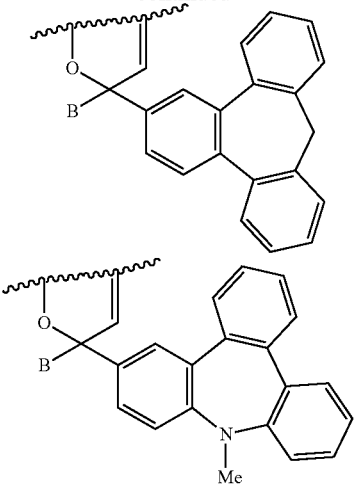

However, it is, of course, also possible that only one benzo ring is present, fused via two adjacent carbon atoms of this V—(CR$_8$R$_9$)$_p$—W moiety.

To synthesize the compounds according to the invention, suitably substituted methylidenesuccinic anhydrides are subjected in a first step to a Friedel-Crafts reaction with suitably substituted benzene derivatives (step (i)). The COOH group of the resulting intermediate is subsequently protected and this intermediate is subjected to a Michael addition with appropriately substituted benzylic Grignard compounds (step (ii)). After removal of the carboxylic acid protecting group, correspondingly substituted derivatives are formed via intramolecular cyclization using phosphoric acid (step (iii)). These substituted derivatives are then reacted with suitably substituted 2-propyn-1-ol derivatives to the inventive compounds according to step (iv). The abovementioned synthetic scheme is depicted in FIG. 1.

To measure the spectral and photochromic properties of the compounds according to the invention, 1.5% by weight of each photochromic dye, together with a commercially available UV initiator of free-radical polymerizations, were dissolved in a viscous liquid acrylate monomer matrix. By means of spin coating or doctor blades, a thin layer of this viscous dye solution was applied to a transparent plastic substrate to give a layer thickness of about 40 μm. The layer was then cured (polymerized) by UV light.

The photochromic properties of the specimens prepared in this way were then determined according to DIN EN ISO 8980-3 (darkening performance at 23° C. under defined exposure conditions).

Figure 2:
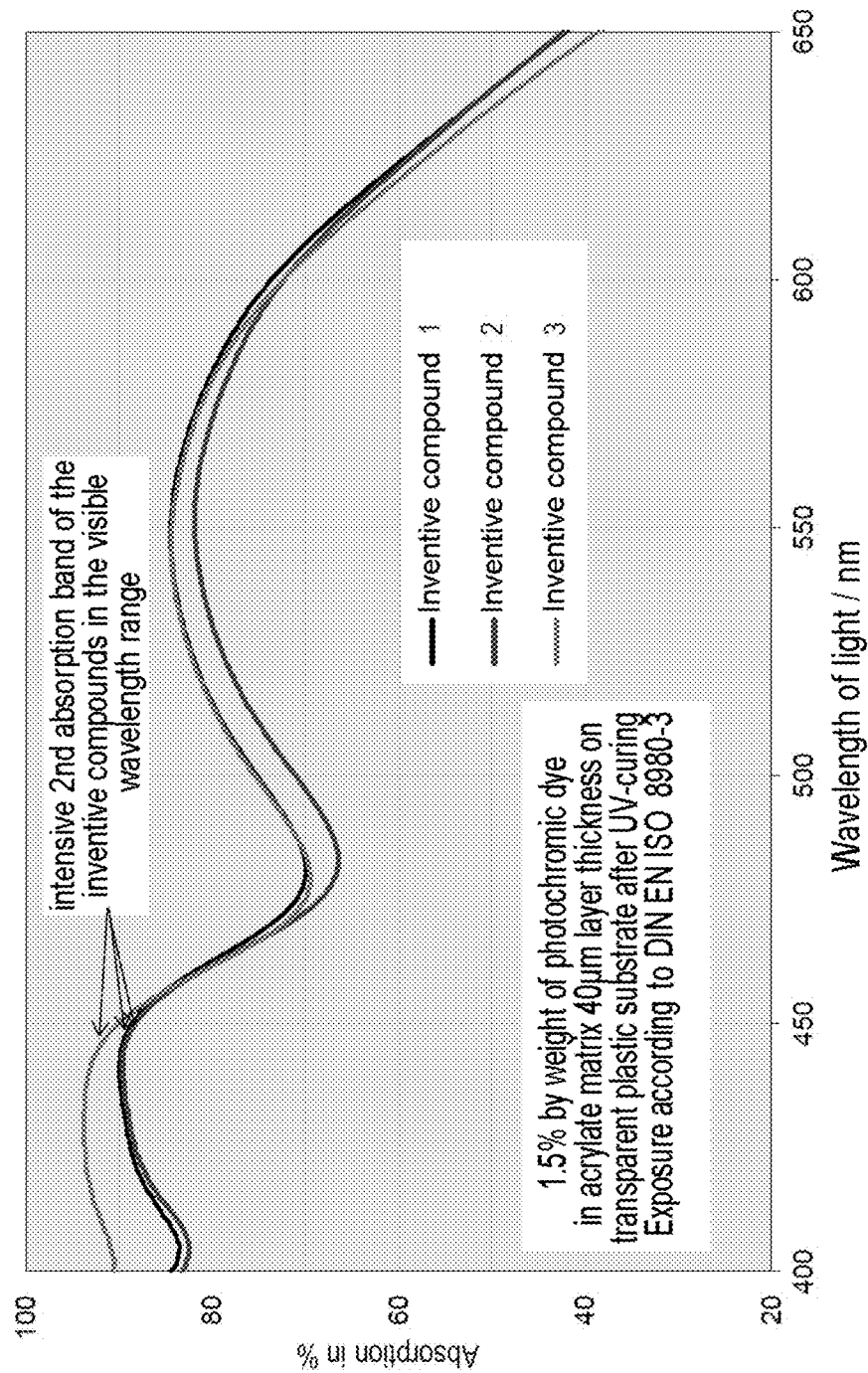
FIG. 2 shows the UV absorption spectra of specific compounds according to the invention in comparison with the prior art.

By way of example, the absorption spectra of selected, inventive compounds in the excited state are shown in FIG. 2. The results of the measurements of the darkening performance according to DIN EN ISO 8980-3 and the lifetime stability are shown in Table 1 below.

The inventive compounds presented in FIG. 2 have the following molecular structure based on formula (III):

|  | R$_1$ | R$_3$ | B | B' |
|---|---|---|---|---|
| Inventive compound 1 | Methyl | H | 4-Methoxyphenyl | 4-Methoxyphenyl |
| Inventive compound 2 | Methyl | Methyl | 4-Methoxyphenyl | 4-Methoxyphenyl |

-continued

| | $R_1$ | $R_3$ | B | B' |
|---|---|---|---|---|
| Inventive compound 3 | Methyl | Methyl | 4-Methoxyphenyl | Phenyl |

The compounds according to the invention have a distinct double absorption band, in which the shorter-wave absorption maximum is somewhat more pronounced than the longer-wave one. This results in brown hues in the darkening.

Table 1 shows a comparison of the darkening performance (i.e. the saturation absorptions from measurements according to DIN EN ISO 8980-3) in the excited state (i.e. directly after UV curing) and also after the lifetime test. To measure the lifetime stability, the specimens are exposed for 50 h to strong UV radiation in an illumination apparatus (simulation of several years of exposure to sunlight).

TABLE 1

Photochromic properties of inventive compounds
(An = anisyl, i.e. the 4-methoxyphenyl residue)

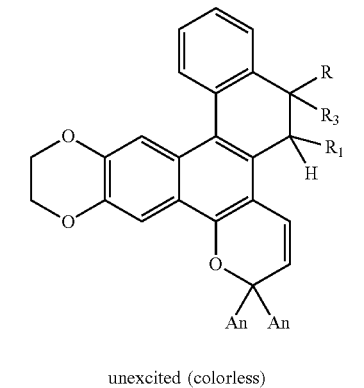

unexcited (colorless)

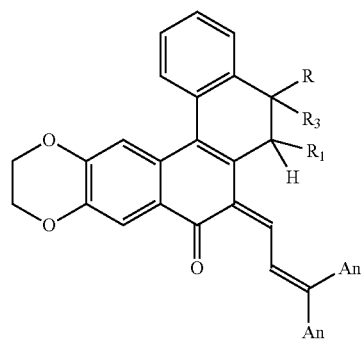

excited (colored)

Table 1 below includes two compounds from the prior art (U.S. Pat. No. 6,506,538) and two non-inventive comparative compounds where R=phenyl and $R_1$=H.

Inventive compounds in Table 1 include only compounds where R=phenyl and at the same time $R_1$=methyl. R corresponds to $R_2$ in the formulae (I) and (II) above.

TABLE 1

| | R | $R_1$ | $R_3$ | Saturation absorption after UV curing | Saturation absorption after lifetime test |
|---|---|---|---|---|---|
| Prior art from U.S. Pat. No. 6,506,538 | H | H | H | 63% | 15% |
| Prior art from U.S. Pat. No. 6,506,538 | H | Methyl | Ethyl | 65% | 47% |
| Comparative compound (non-inventive) | Phenyl | H | H | 64% | 44% |
| Comparative compound (non-inventive) | Phenyl | H | Phenyl | 65% | 49% |
| Inventive compound 1 | Phenyl | Methyl | H | 77% | 73% |
| Inventive compound 2 | Phenyl | Methyl | Methyl | 78% | 76% |

As Table 1 clearly shows, only the UV-cured specimens with the inventive compounds have satisfactory UV curing and lifetime stability for commercial UV-cured phototropic ophthalmic lenses, i.e. these specimens show only a very marginal loss of the saturation absorption after the lifetime test.

Firstly, in the compounds from the prior art and the non-inventive comparative compounds, a lower saturation absorption could already be observed compared to the inventive compounds prior to the lifetime test—these compounds already partially decompose in the brief but strong irradiation with UV light during the UV curing. Secondly, after the lifetime test, these compounds show a further, drastic loss of saturation absorption which renders them unsuitable for use in UV-cured phototropic ophthalmic lenses.

The reason for the drastically increased UV curing and lifetime stability compared to the compounds from the prior art lies in the combination according to the invention of the introduction of a phenyl substituent R together with the introduction of a further substituent $R_1$ on the adjacent carbon atom (a methyl group in Table 1).

The compounds according to the invention may be used in plastic materials or plastic items of every type and form for a variety of purposes for which photochromic behavior is of interest. Here, a dye according to the present invention or a mixture of such dyes may be used. For example, the photochromic naphthopyran dyes according to the invention may be used in lenses, particularly ophthalmic lenses, glasses for eyewear of all types, such as ski goggles, sunglasses, motorcycle goggles, visors of helmets and the like. Furthermore, the photochromic naphthopyrans according to the invention can also be used, for example, as sun protection in vehicles and homes in the form of windows, protective screens, covers, roofs and the like.

For the preparation of such photochromic items, the photochromic naphthopyrans according to the invention can be applied to, or embedded in, a polymeric material, such as an organic plastic material, by various methods described in the prior art, such as already indicated in WO 99/15518.

We distinguish here between so-called mass coloring and surface staining procedures. A mass coloring procedure comprises, for example, the dissolving or dispersing of the photochromic compound or compounds according to the present invention in a plastic material, for example, by the addition of the photochromic compound(s) to a monomeric material before the polymerization is carried out. A further possibility for producing a photochromic item is to permeate the plastic material(s) with the photochromic compound(s) by immersing the plastic material(s) in a hot solution of the photochromic dye(s) according to the present invention or, for example, by a thermal transfer process. The photochromic compound(s) may also be provided, for example, in the form of a separate layer between adjacent layers of the plastic material, for example, as part of a polymeric film. Further, it is also possible to deposit the photochromic compound(s) as part of a coating present on the surface of the plastic material. The term "permeation" here is intended to mean the migration of the photochromic compound(s) into the plastic material, for example, by the solvent-assisted transfer of the photochromic compound(s) into a polymer matrix, vapor phase transfer or other such surface diffusion processes. Advantageously, such photochromic items, such as ophthalmic lenses, can be produced not only by means of conventional mass coloring, but also in the same manner by means of surface staining, where in the latter variant a surprisingly lower migration tendency can be achieved. This is a particular advantage in the subsequent processing steps, since—for example, as with an antireflective coating due to the lower back diffusion in a vacuum—delamination and similar defects are drastically reduced.

Overall, based on the photochromic naphthopyrans according to the invention, any compatible (in chemical terms and in a color-dependent manner) stains, i.e. dyes, may be applied to, or embedded in, the plastic material in order to satisfy both aesthetic aspects and medical or fashion aspects. The specifically selected dye(s) may therefore vary, depending on the intended effects and requirements.

The invention claimed is:

1. A photochromic fused naphthopyran according to the general formula (III):

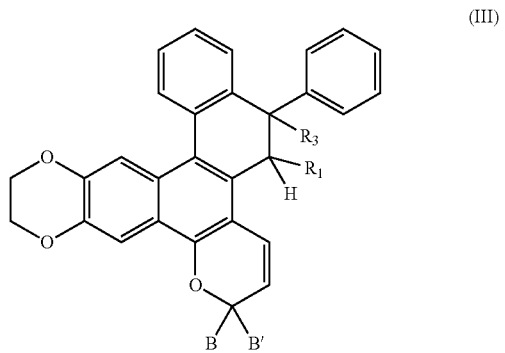

(III)

where the residue $R_1$ is a $(C_1-C_6)$-alkyl residue or a phenyl residue;

the residue $R_3$ is hydrogen, a $(C_1-C_6)$-alkyl residue or a phenyl residue; and and where B and B' are mutually independently selected from one of the following groups a) or b), where a) is an unsubstituted, mono-, di- and trisubstituted aryl residue, wherein the aryl residue is phenyl, naphthyl or phenanthryl and b) is an unsubstituted, mono- and disubstituted heteroaryl residue, wherein the heteroaryl residue is pyridyl, furanyl, thienyl, benzofuranyl, benzothienyl, 1,2,3,4-tetrahydrocarbazolyl and julolidinyl;

wherein the substituents of the aryl and heteroaryl residues in a) and b) are selected from the group α consisting of a hydrogen atom, a $(C_1-C_6)$-alkyl residue, a $(C_1-C_6)$-thioalkyl residue, a $(C_3-C_7)$-cycloalkyl residue which may have one or more heteroatoms such as O or S, a $(C_1-C_6)$-alkoxy residue, a hydroxyl group, a trifluoromethyl group, bromine, chlorine, fluorine, an unsubstituted, mono- or disubstituted phenyl, phenoxy, benzyl, benzyloxy, naphthyl or naphthoxy residue, or from the group χ consisting of amino, mono-$(C_1-C_6)$-alkylamino, di-$(C_1-C_6)$-alkylamino, phenethenyl unsubstituted, mono- or disubstituted on the phenyl ring, unsubstituted, mono- or disubstituted (phenylimino)methylene, unsubstituted, mono- or disubstituted (phenylmethylene)imino and unsubstituted, mono- or disubstituted mono- and diphenylamino, piperidinyl, 3,5-dimethylpiperidinyl, N-substituted piperazinyl, pyrrolidinyl, imidazolidinyl, pyrazolidinyl, indolinyl, morpholinyl, 2,6-dimethylmorpholinyl, thiomorpholinyl, azacycloheptyl, azacyclooctyl, unsubstituted, mono- or disubstituted phenothiazinyl, unsubstituted, mono- or disubstituted phenoxazinyl, unsubstituted, mono-, di- or trisubstituted 9,10-dihydroacridinyl, unsubstituted, mono- or disubstituted 1,2,3,4-tetrahydroquinolinyl, unsubstituted, mono- or disubstituted 2,3-dihydro-1,4-benzoxazinyl, unsubstituted, mono- or disubstituted 1,2,3,4-tetrahydroisoquinolinyl, unsubstituted, mono- or disubstituted phenazinyl, unsubstituted, mono- or disubstituted carbazolyl, unsubstituted, mono- or disubstituted 1,2,3,4-tetrahydrocarbazolyl and unsubstituted, mono- or disubstituted 10,11-dihydrodibenz[b,f]azepinyl, wherein the substituent(s) may in turn be mutually independently selected from the group α;

or wherein two directly adjacent substituents of the aryl and heteroaryl residues in a) and b) are a V—$(CR_8R_9)_p$—W moiety, where p=1, 2 or 3, the residues $R_8$ and $R_9$ are each mutually independently a substituent selected from the group α, and also V and W are mutually independently selected from the moieties —O—, —S—, —N($C_1-C_6$)-alkyl, —NC$_6$H$_5$-, —CH$_2$—, —C(CH$_3$)$_2$—or —C(C$_6$H$_5$)$_2$—;

or two or more adjacent —CR$_8$R$_9$ moieties are part of a fused benzene ring, which may be unsubstituted, mono- or disubstituted, wherein the substituents may in turn be selected from the group α;

or V and/or W together with the respective adjacent —CR$_8$R$_9$ moiety is a fused benzene ring, which may be unsubstituted, mono- or disubstituted, wherein the substituents may in turn be selected from the group α.

2. The photochromic fused naphthopyran as claimed in claim 1, which are:

3,3-bis(4-methoxyphenyl)-6,7-ethylenedioxy-13-phenyl-14-methyl-13,14-dihydro-naphtho[2,1-d]naphtho[1,2-b]pyran;

3,3-bis(4-methoxyphenyl)-6,7-ethylenedioxy-13-phenyl-13,14-dimethyl-13,14-dihydro-naphtho[2,1-d]naphtho[1,2-b]pyran;

3,3-bis(4-ethoxyphenyl)-6,7-ethylenedioxy-13-phenyl-14-methyl-13,14-dihydro-naphtho[2,1-d]naphtho[1,2-b]pyran;

3,3-bis(4-ethoxyphenyl)-6,7-ethylenedioxy-13-phenyl-13,14-dimethyl-13,14-dihydro-naphtho[2,1-d]naphtho[1,2-b]pyran;

3-(4-methoxyphenyl)-3-phenyl-6,7-ethylenedioxy-13-phenyl-14-methyl-13,14-dihydro-naphtho[2,1-d]naphtho[1,2-b]pyran;

3-(4-methoxyphenyl)-3-phenyl-6,7-ethylenedioxy-13-phenyl-13,14-dimethyl-13,14-dihydro-naphtho[2,1-d]naphtho[1,2-b]pyran;

3-(4-ethoxyphenyl)-3-phenyl-6,7-ethylenedioxy-13-phenyl-14-methyl-13,14-dihydro-naphtho[2,1-d]naphtho[1,2-b]pyran;

3-(4-ethoxyphenyl)-3-phenyl-6,7-ethylenedioxy-13-phenyl-13,14-dimethyl-13,14-dihydro-naphtho[2,1-d]naphtho[1,2-b]pyran;

3-(4-butoxyphenyl)-3-phenyl-6,7-ethylenedioxy-13-phenyl-14-methyl-13,14-dihydro-naphtho[2,1-d]naphtho[1,2-b]pyran; or 3-(4-butoxyphenyl)-3-phenyl-6,7-ethylenedioxy-13-phenyl-13,14-dimethyl-13,14-dihydro-naphtho[2,1-d]naphtho[1,2-b]pyran.

3. The photochromic fused naphthopyran as claimed in claim 1, wherein the residues B and B' are mutually independently selected from the group a), as defined above.

4. A plastic material comprising the photochromic fused naphthopyran as claimed in claim 1, wherein the photochromic material is disposed in the plastic material, disposed in a coating on a surface of the plastic material, or provided as a separate layer disposed between adjacent layers of the plastic material.

5. The plastic material as claimed in claim 4, wherein the plastic material is an ophthalmic lens.

* * * * *